United States Patent [19]

Thomas, Jr.

[11] 4,420,311
[45] Dec. 13, 1983

[54] DIESEL FUEL COMPOSITION
[75] Inventor: Samuel G. Thomas, Jr., Rochester, Mich.
[73] Assignee: Ethyl Corporation, Richmond, Va.
[21] Appl. No.: 440,182
[22] Filed: Nov. 9, 1982
[51] Int. Cl.³ ............................................... C10L 1/22
[52] U.S. Cl. .......................................... 44/53; 44/56; 44/57; 260/466
[58] Field of Search ................ 44/53, 56, 57; 260/466
[56] References Cited
U.S. PATENT DOCUMENTS 2,905,540  9/1959  Schickh et al. ......................... 44/57
2,955,409  9/1959  Von Schickh et al. ................ 44/57
4,198,931  4/1980  Malec .................................... 44/56
4,204,481  5/1980  Malec .................................... 44/56
4,227,889 10/1980  Perilstein .............................. 44/56
4,248,182  2/1981  Malec .................................... 44/56
4,359,324 11/1982  Elsea, Jr. et al. ..................... 44/57

Primary Examiner—John Doll
Assistant Examiner—Y. Harris-Smith
Attorney, Agent, or Firm—Donald L. Johnson; John F. Sieberth; Joseph D. Odenweller

[57] ABSTRACT

The cetane number of diesel fuel is increased by the addition of a small amount of a cyclododecyl nitrate.

2 Claims, No Drawings

DIESEL FUEL COMPOSITION

BACKGROUND

Diesel engines operate by compression ignition. They have compression ratios in the range of 14:1 to 17:1 or higher and for that reason obtain more useful work from a given amount of fuel compared to an Otto cycle engine. Historically, diesel engines have been operated on a petroleum-derived liquid hydrocarbon fuel boiling in the range of about 300°–750° F. Recently, because of dwindling petroleum reserves, alcohol and alcohol-hydrocarbon blends have been studied for use as diesel fuel.

One major factor in diesel fuel quality is cetane number. Cetane number is related to ignition delay after the fuel is injected into the combustion chamber. If ignition delays too long, the amount of fuel in the chamber increases and upon ignition results in a rough running engine and increased smoke. A short ignition delay results in smooth engine operation and decreases smoke. Commercial petroleum diesel fuels generally have a cetane number of about 40–55. Alcohols have a much lower cetane value and require the addition of a cetane improver for successful engine operation.

Through the years, many types of additives have been used to raise the cetane number of diesel fuel. These include peroxides, nitrites, nitrates, nitrosocarbamates, and the like. Alkyl nitrates such as amyl nitrate, hexyl nitrate and mixed octyl nitrates have been used commercially with good results. Likewise, $C_{5-8}$ cycloalkyl nitrates are reported to be an effective cetane improver (U.S. Pat. No. 2,905,540).

SUMMARY

It has now been discovered that cyclododecyl nitrate is a very effective cetane improver even at very low concentrations.

DESCRIPTION OF PREFERRED EMBODIMENT

A preferred embodiment of the invention is liquid fuel adapted for use in a diesel engine, said fuel being selected from the group consisting of liquid hydrocarbons of the diesel boiling range, alcohols and mixtures thereof, said fuel containing a cetane increasing amount of an additive of the formula

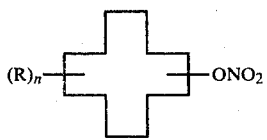

wherein R is selected from the group consisting of hydrogen, alkyl containing 1–12 carbon atoms and alkoxy containing 1–12 carbon atoms and n is an integer from 0 to 3.

Representative examples of these additives are:
4-methyl cyclododecyl nitrate
4-ethyl cyclododecyl nitrate
4-isobutyl cyclododecyl nitrate
4-(2-ethylhexyl) cyclododecyl nitrate
6-n-dodecyl cyclododecyl nitrate
6-methyl cyclododecyl nitrate
4-ethoxy cyclododecyl nitrate
3-isobutoxy cyclododecyl nitrate
3-dodecyloxy cyclododecyl nitrate The most preferred additive is the compound cyclododecyl nitrate. This compound is reported at *Chem. Abst.* 58, 2380d.

The additives can be readily made by nitration of the corresponding cyclododecyl alcohol using a mixed nitric-sulfuric acid or a mixed nitric-acetic anhydride. The following examples illustrates the method of making the additives.

EXAMPLE 1

In a reaction vessel was placed 40 ml. acetic acid. This was stirred and cooled to $-14°$ C. and then 10.5 ml. 90 percent fuming nitric acid was added while keeping the temperature below $-7°$ C. Then, 0.2 g. urea was added following which 27.6 g. (0.15 mole) of cyclododecanol was added at $-14°$ C. to $-5°$ C. over an one-hour period. The mixture was stirred 1.5 hours at $-5°$ to $-7°$ C. and then poured into an ice-water mixture. The entire aqueous mixture was extracted with diethyl ether and the ether extract was washed with aqueous sodium carbonate and then dried over anhydrous sodium sulfate. The ether was evaporated off at 30° C. per 30 mm. Hg leaving 33.83 g. of white solid identified by IR as predominantly cyclododecyl nitrate.

Other cyclododecyl nitrates can be made following the above general procedure by substituting different cyclododecanols.

The amount of cetane improver added depends on the type of fuel being used, the initial cetane value, and the amount of cetane number increase desired. Alcohol fuels such as methanol, ethanol, isopropanol, isobutanol, hexanol, and the like, have very low cetane values and large amounts of cetane improvers are required. A useful range in which to operate is about 5–25 weight percent cetane improver.

Blends of alcohol and petroleum-derived diesel fuel have higher cetane values and require less cetane improver. A useful range is about 0.5–10 weight percent.

Petroleum-derived distillate fuels in the diesel boiling range require only small amounts of cetane improver to achieve a significant increase in cetane number. Such fuels without any cetane improver generally have cetane numbers in the range of about 25–60. Cetane numbers in the range of 25–35 are considered low and those in the range of 50–60 are considered top grade diesel fuels. Diesel fuels in the 35–50 mid-range are most common. An object of the invention is to upgrade the low cetane number fuels at least into the mid-range and to increase the cetane value of the mid-range fuels into the upper portion of the mid-range (e.g. 45–50) or even into the premium range above 50. It has been found that highly beneficial results can be achieved using as little as 0.05 weight percent of the present additive. Accordingly, a useful concentration range in petroleum derived diesel fuel is about 0.01–5 weight percent and more preferably about 0.05–0.5 weight percent.

The cetane increase caused by the present additive was measured using a standard cetane engine in comparison with the increase caused by cyclohexyl nitrate. The fuel was a blend of 28 cetane number light cycle oil and 46 cetane number diesel fuel giving a blend of slightly over 38 cetane number.

| Concentration | Cyclohexyl Nitrate | | Cyclododecyl Nitrate | |
| --- | --- | --- | --- | --- |
| | CN | Increase | CN | Increase |
| None | 38.33[1] | — | 38.25[2] | — |
| 0.05 wt. percent | 40.02 | 1.69 | 40.77 | 2.52 |
| 0.10 wt. percent | 41.47 | 3.14 | 42.02 | 3.77 |
| 0.15 wt. percent | 42.69 | 4.36 | 43.13 | 4.88 |

[1] average of 2 runs
[2] average of 2 runs

The increase in cetane number (CN) is measured against the baseline (none). The two baselines are slightly different because, although the fuels were identical, each test series was run on a different day.

The results show that the cyclododecyl nitrate was much more effective compared to the cyclohexyl nitrate. At 0.15 wt. percent, it was 12 percent more effective. At 0.10 wt. percent, it was 20 percent more effective. At 0.05 wt. percent, the cyclododecyl nitrate was a surprising 49 percent more effective than cyclohexyl nitrate.

Other conventional additives may be included in the diesel fuel including antioxidants, pour point depressants, cold flow improvers, cold filter plugging inhibitors, detergents, rust inhibitors and the like, including other cetane improvers.

I claim:

1. Liquid fuel adapted for use in a diesel engine, said fuel being selected from the group consisting of liquid hydrocarbons of the diesel boiling range, alcohols and mixtures thereof, and said fuel containing a cetane increasing amount of an additive of the formula

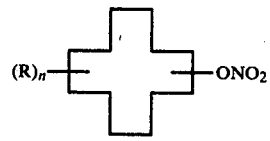

wherein R is selected from the group consisting of hydrogen, alkyl containing 1-12 carbon atoms and alkoxy containing 1-12 carbon atoms and n is an integer from 0 to 3.

2. A fuel composition of claim 1 wherein said additive is the compound cyclododecyl nitrate.

* * * * *